United States Patent [19]

Simpson

[11] Patent Number: Plant 6,606

[45] Date of Patent: Feb. 14, 1989

[54] CANDYMINT SARGENT CRABAPPLE TREE

[75] Inventor: Thomas R. Simpson, Vincennes, Ind.

[73] Assignee: Simpson Orchard Company, Inc., Vincennes, Ind.

[21] Appl. No.: 98,322

[22] Filed: Sep. 18, 1987

[51] Int. Cl.[4] ..... A01H 5/03
[52] U.S. Cl. ..... Plt./34
[58] Field of Search ..... Plt./34

*Primary Examiner*—Robert E. Bagwill
*Attorney, Agent, or Firm*—Charles W. Rummler

[57] ABSTRACT

A new variety of Sargent crabapple tree particularly distinguished by its relatively short, low spreading and very horizontal form and a foliage coloration that is of a darker purplish green than the light green of the normal Sargent variety. The flowers of this new Sargent variety open to red to light pink with a red edging on the petals instead of the pure white flowers of the normal Sargent variety. This new crabapple tree flowers profusely and with its low horizontal form, the tree has a definite Oriental flavor quite unlike any other crabapple tree known to applicant.

2 Drawing Sheets

BACKGROUND OF THE INVENTION

This new crabapple variety originated as a seedling of unknown parentage which I discovered in my nursery during the summer of 1979 and which I particularly noted, from about three thousand other Sargent crabapple trees growing in my nursery, because of its vigorous growth and reddish green leaves and a growth habit that was extremely horizontal, unlike any other crabapple tree that I know of. Because of its vigorous and low spreading growth habit, I propagated this discovery tree by budding in 1979 with very satisfactory results at my nursery at Vincennes, Ind., and further propagation of this new variety in the same manner shows that its novel characteristics will hold true from generation to generation and appear to be firmly fixed.

A row of first budded trees of this new crabapple variety now average about six to eight feet high, each with a spread of about twelve feet. The bark of this new tree is of a reddish color, similar in appearance to that of a cherry tree.

DESCRIPTION OF THE DRAWING

My new variety of Sargent crabapple tree is illustrated by the accompanying drawings, of which sheet one shows, in its upper view, a tree of the new variety in full bloom, and the lower view shows an elevational view of one of the new trees and illustrates its relatively low height and very wide spreading appearance. Sheet two of the drawings, in the upper view, illustrates a branch of the new crabapple variety showing its fully budded form just prior to the opening of its flowers, and the lower view is a close-up of a group of the flowers illustrating their form and general coloration, the colors shown being as close to those herein specified as can be reasonably obtained by professional photographic procedures.

DESCRIPTION OF THE NEW PLANT

The following is a detailed description of my new Sargent crabapple variety as observed at my nursery in Vincennes, Ind., during the spring and summer of 1987, the color designations being according to The R.H.S. Colour Chart published by The Flower Council of Holland in collaboration with The Royal Horticultural Society of London, England.

THE PLANT

Form: Small, low spreading tree.
Height: About 8 to 10 feet.
Trunk size: About 8 to 10 inches.
Bark: Smooth.
Growth rate: Moderate with good strength.
Branches:
- *Number.*—Numerous.
- *Size.*—Relatively small and closely spaced.
- *Angle of attachment.*—Generally about 90° and recurred to horizontally outward projection.
- *Bark.*—Dark Reddish Brown, about 200 B.
- *Lenticels.*—Size: Medium. Quantity: Widely spaced.

Foliage:
- *Quantity.*—Abundant.
- *Leaf size.*—Length — Up to about 4¼ inches. Width — Up to about 3½ inches.
- *Form.*—Simple to lobed with serrate margins.
- *Texture.*—Leathery.
- *Color.*—Upper side — Purplish Green, 146 A, to Reddish Brown, 200 C. Under side — Lighter Green, 148 A to 200 D.
- *Leaflets.*—Number: Two. Size: Small.
- *Petioles.*—Length: About ¾ inch.
- *Ribs and veins.*—Color: Red.
- *Thorns, spines and prickles.*—None.

FLOWER BUDS

Form: Round.
Size: Small.
- *Diameter.*—About ⅜ inch.

Opening rate: Slow, over a long period.
Color:
- *When sepals first divide.*—Very Deep Reddish Purple, 60 A.
- *When petals begin to unfurl.*—Red-Purple, 63 A.

Sepals: Hooded over the bud and curl back as the flower opens.
- *Color.*—Inside — Reddish green. Outside — Reddish green.

Calyx:
- *Shape.*—Round.
- *Size.*—About ⅜ inch.
- *Aspect.*—Smooth.

*Splitting.*—The calyx does not split.

Peduncle:

*Length.*—About $\frac{7}{8}$ inch.

*Color.*—Red.

*Character.*—Quite stiff.

THE FLOWERS

Blooming period: Mid to late spring.

Quantity: Profuse.

Size: Medium.

*Diameter.*—About $1\frac{1}{4}$ inch.

*Depth.*—About $\frac{3}{8}$ inch.

Borne: Singly.

Shape:

*When first opening.*—Cup-shaped.

*As bloom matures.*—The flower flattens out.

Petalage:

*Number of petals.*—Five.

*Arrangement.*—Cymose.

*Form.*—Oval.

*Margin.*—Entire.

*Color.*—All petals — Pale Pink to Deep Pink, 65 D, with Red marginal edges.

*Texture.*—Soft.

*Aspect.*—Velvety.

Peduncle:

*Length.*—About $\frac{7}{8}$ inch.

*Color.*—Red.

*Character.*—Stiff.

Fragrance: Slightly sweet.

THE REPRODUCTIVE ORGANS

Stamens: About 15.

*Arrangement.*—Circular.

*Anthers.*—Length: About 1/16 inch.

*Filaments.*—Length: About $\frac{1}{4}$ inch. Color: Reddish.

*Pollen.*—Color: Pale Yellow.

Pistils:

*Number.*—One.

*Length.*—About $\frac{1}{4}$ inch.

THE FRUIT

Maturity period: Late season and persistent.

Size: Medium and uniform.

*Axial diameter.*—About 7/16 inch.

*Transverse diameter.*—About 9/16 inch.

Form: Oblate.

Cavity.—Round.

*Depth.*—Shallow.

*Breadth.*—About $\frac{1}{8}$ inch.

*Stem.*—Size: About $\frac{7}{8}$ inch.

*Basin.*—Shape: Round. Depth: Shallow. Breadth: About 150 inch. Markings: Large scar.

*Skin.*—Thickness: Thick. Texture: Smooth. Lenticels: None. Color: Deep purple.

*Flesh.*—Texture: Hard. Juice: Dry. Flavor: Tart. Aroma: None. Color: Greenish.

*Core.*—Bundle area: About $\frac{1}{4}$ inch. Shape: Round. Color: A Reddish cast.

*Seeds.*—Number: One or two. Length: About 3/16 inch. Breadth: About $\frac{1}{8}$ inch. Color: Light Brown.

I claim:

1. The new and distinctive Sargent crabapple tree and parts thereof, substantially as herein shown and described, particularly characterized by its relatively short height and its low spreading and very horizontal form, and its foliage being of a purplish green coloration, darker than that of a normal Sargent variety.

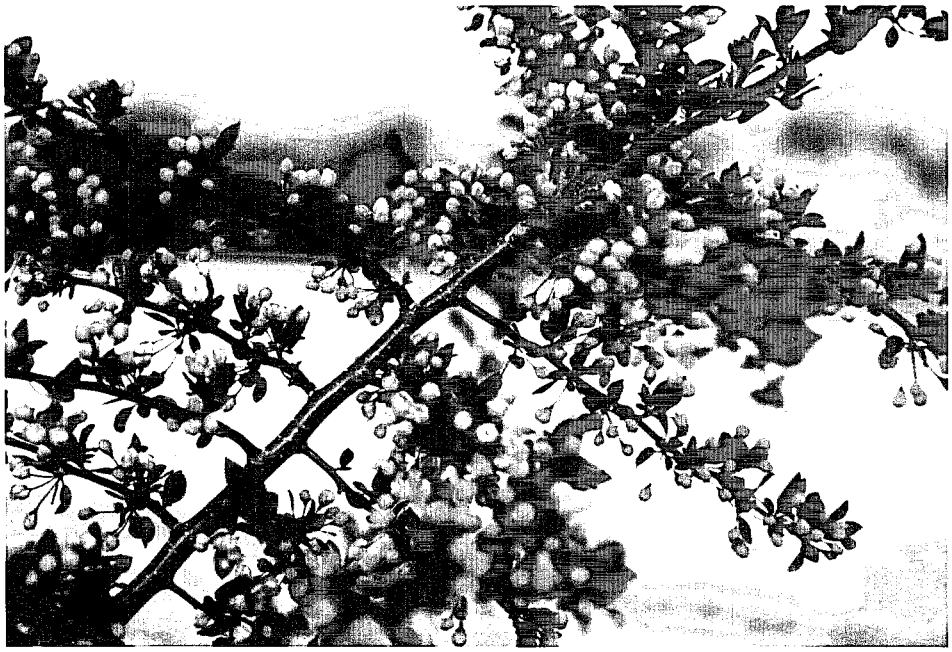
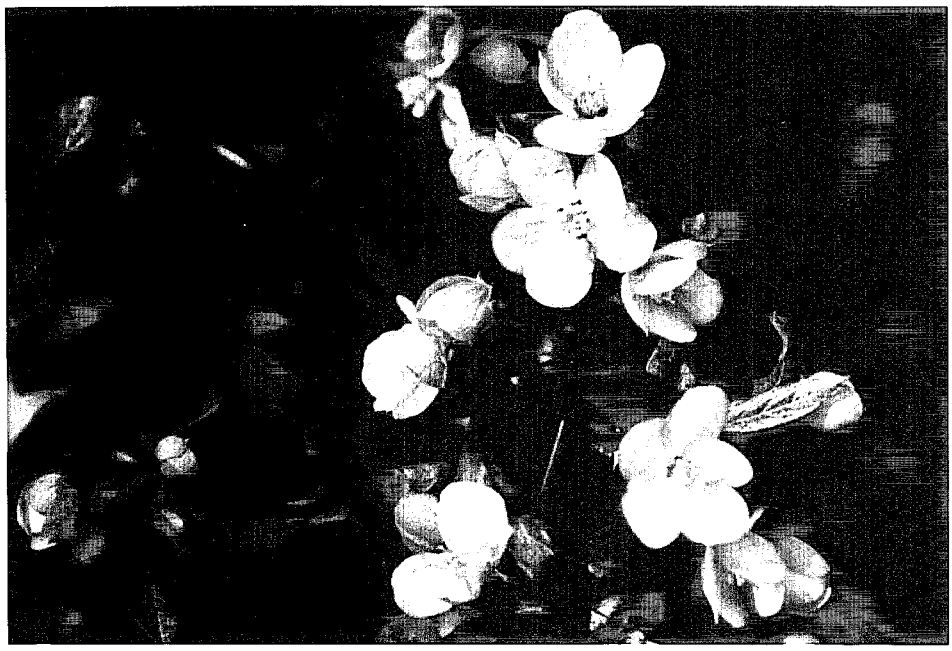

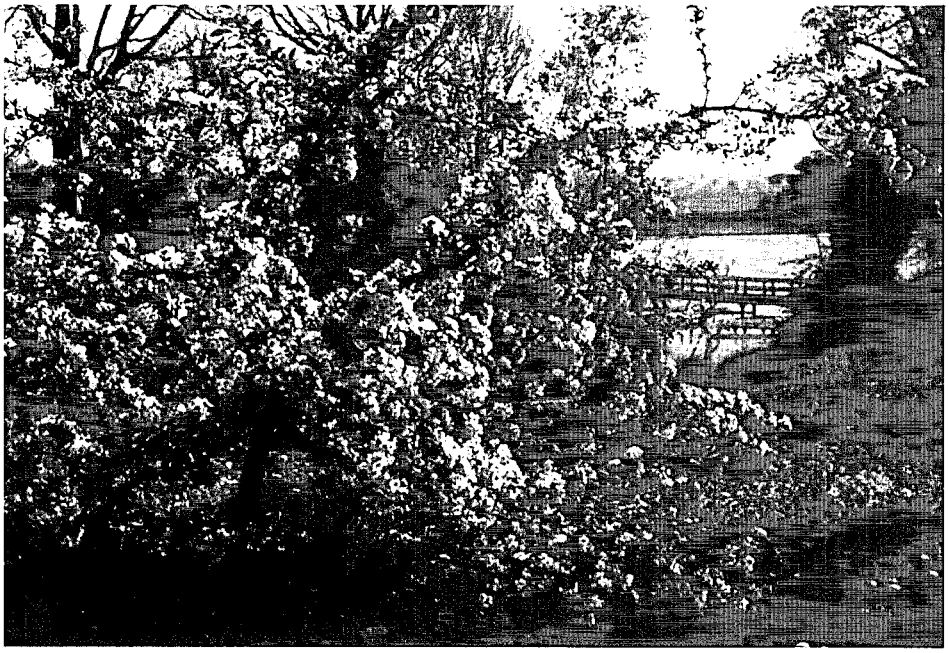
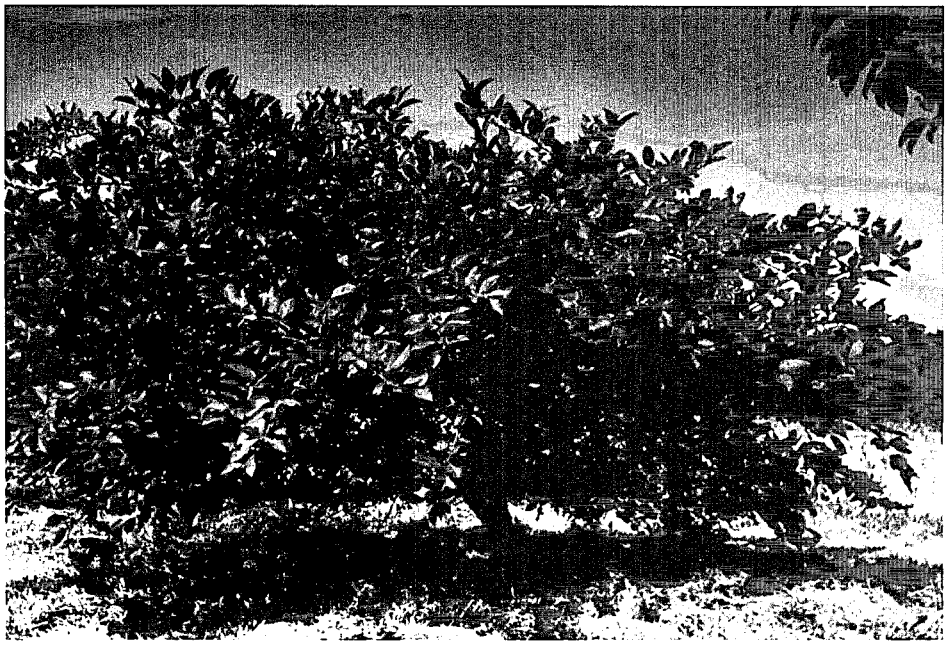

* * * * *